United States Patent [19]

Luksha

[11] Patent Number: 4,679,562

[45] Date of Patent: Jul. 14, 1987

[54] GLUCOSE SENSOR

[75] Inventor: Eugene Luksha, Golden Valley, Minn.

[73] Assignee: Cardiac Pacemakers, Inc., St. Paul, Minn.

[21] Appl. No.: 861,347

[22] Filed: May 9, 1986

Related U.S. Application Data

[63] Continuation of Ser. No. 466,881, Feb. 16, 1983, abandoned.

[51] Int. Cl.$^4$ .............................................. A61B 5/00
[52] U.S. Cl. .................................... 128/635; 204/415
[58] Field of Search ............... 128/635; 204/409, 415, 204/195 B, 195 P

[56] References Cited

U.S. PATENT DOCUMENTS

| | | |
|---|---|---|
| 3,519,538 | 7/1970 | Messing et al. . |
| 3,539,455 | 11/1970 | Clark, Jr. . |
| 3,542,662 | 11/1970 | Hicks et al. . |
| 3,556,945 | 1/1971 | Messing . |
| 3,666,627 | 5/1972 | Messing . |
| 3,783,101 | 1/1972 | Tomb et al. . |
| 3,839,175 | 10/1974 | Keyes . |
| 3,902,970 | 9/1975 | Levin . |
| 4,085,009 | 4/1978 | Pace . |
| 4,129,478 | 12/1978 | Racine et al. . |
| 4,276,144 | 6/1981 | Hahn et al. ........................ 128/635 |
| 4,442,841 | 4/1984 | Uehara et al. ..................... 128/635 |

Primary Examiner—Edward M. Coven
Attorney, Agent, or Firm—Orrin M. Haugen; Thomas J. Nikolai

[57] ABSTRACT

A glucose sensor for electrically determining blood glucose concentration for in vivo and in vitro applications and comprising an iridium substrate with an oxidized surface, to which is bonded a first film of silanized gamma propyltriethoxysilane and a second film of glucose oxidase covalently bonded thereto. The electrode provides an electrial signal, the amplitude of which varies in response to changes in blood glucose concentration, with the electrode being both rugged and stable.

6 Claims, 1 Drawing Figure

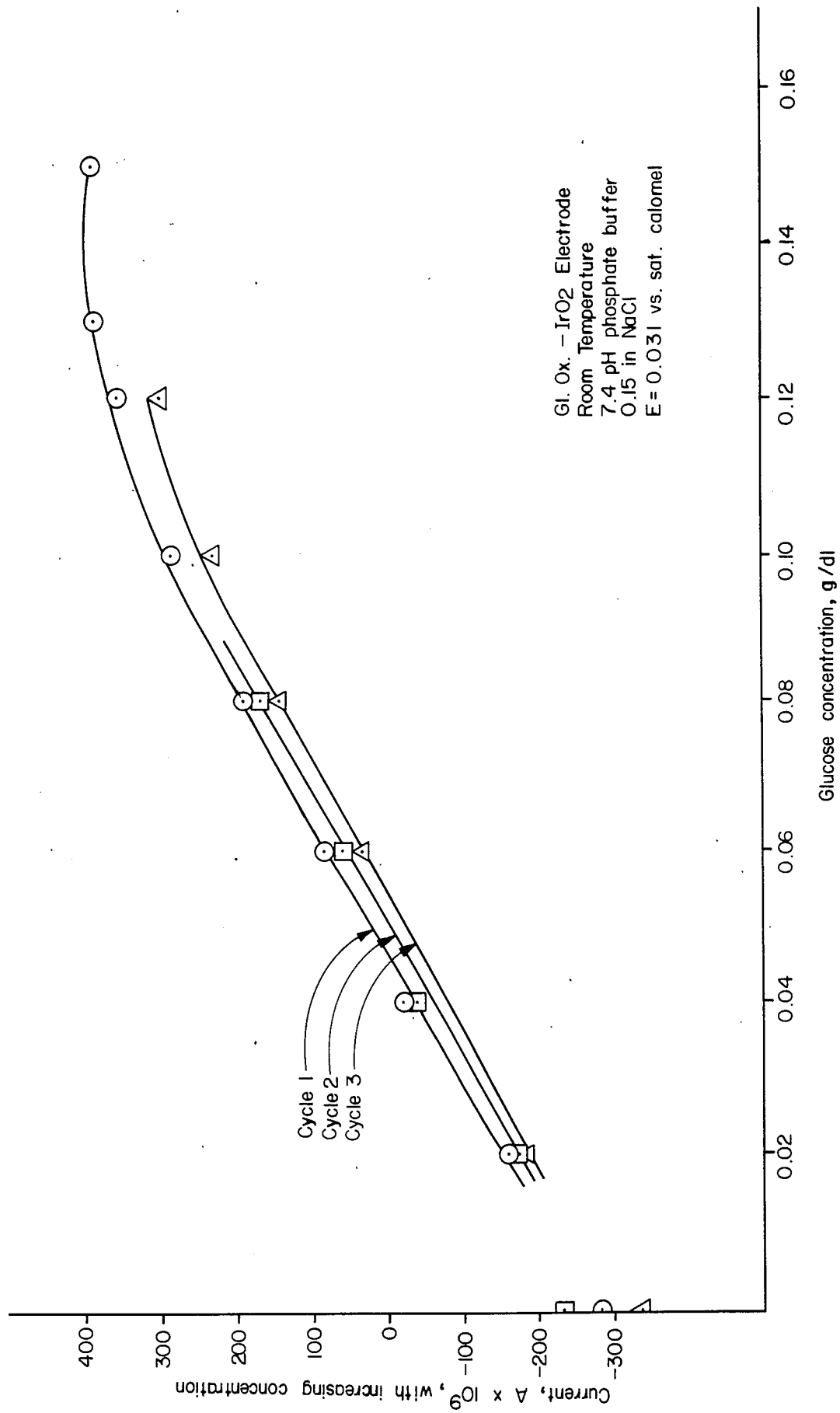

GLUCOSE SENSOR

This is a continuation of application Ser. No. 06/466,881, filed Feb. 16, 1983 now abandon.

BACKGROUND OF THE INVENTION

The present invention relates generally to an electrode for sensing and/or determining constituents of blood, and more particularly to such an electrode which provides a stable and rugged detection mechanism adapted to determine glucose levels in blood either in-vivo or in-vitro applications. The electrode consists essentially of a silanized iridium oxide substrate having a glucose oxidase film covalently bonded thereto. A protective overcoating layer or film, permeable to glucose and oxygen is utilized as well, the overcoat film protecting the surface of the covalently bonded oxidase film from direct contact with blood, while having good transport properties for the glucose and oxygen constituents of the blood.

The determination of glucose levels in blood is useful in a variety of applications. One particular application is for use by diabetics in combination with an implantable insulin infusion pump system. The use of implantable insulin pumps is frequently indicated for patients, particularly those diabetics whose conditions are best treated or stabilized by the use of implantable insulin infusion pumps. Glucose sensors are useful in combination with such pumps, since these sensors may be used to determine glucose levels and provide information useful to the system to monitor the administration of insulin in response to actual and/or anticipated changes in blood glucose levels. For example, glucose levels are known to change in response to food and beverage intake, as well as to normal metabolic function. While certain diabetics are able to maintain proper glucose-insulin levels with conventional insulin injection or other insulin administration techniques, some individuals experience unusual problems giving rise to the need for a substantially constant glucose monitoring system to maintain an appropriate glucose-insulin balance in their bodies. The electrode of the present invention provides a means for determining the immediate level of glucose in the blood, with the determination being useful in controlling the glucose level at a specific future or anticipated point in time. In this fashion, glucose levels may be controllably adjusted or otherwise implemented into the anticipated normal activity of the individual whose system is being monitored. Consideration is given to time lags which are inherent in all bodily functions, particularly the metabolic processes, thereby providing a means to achieve a proper insulin-glucose balance on an extended time basis. Through use of the sensor of the present invention, glucose and/or insulin levels may be maintained in proper balance and at desired and appropriate levels, by means of timely infusion of appropriate amounts of insulin to the patient's system.

Glucose levels in the bloodstream of a patient vary on a time basis and are normally dependent upon the physical activity of the individual, his food, beverage and sugar intake, his metabolic rate, along with other factors. Accordingly, changes in the insulin-glucose balance occur in direct response to these time dependent variables. Certain implantable insulin infusion pumps are capable of operation at variable and/or programmable delivery rate, with these rates varying in response to increases and decreases in the sensed as well as the desired glucose level. Stated another way, variable rate infusion pumps deliver insulin at a rate determined in part by the immediate glucose level in the blood, and a glucose sensor is utilized to provide information in the form of a signal indicative of the immediate glucose level in the patient's system. Other factors or information useful for the operation of variable rate infusion pumps include dietary and physical activity with both immediate past activity and anticipated activity being considered pertinent. A properly programmed infusion pump will utilize such information and more in order to perform its function and assist the patient in maintaining a proper insulin balance in his system over an extended period of time.

Glucose, as a compound, is difficult to determine on a direct basis electrochemically, since its properties lead to relatively poor behavior during oxidation and/or reduction activity. Furthermore, glucose levels in blood are difficult to determine inasmuch as most mechanisms for sensing and/or determining glucose levels are affected by the presence of other constituents or compounds normally found in blood. For these reasons, it has been found desirable to utilize various enzymes and/or other protein materials which provide specific reactions with glucose and yield readings and/or by-products which are capable of analyses quantitatively. Accordingly, a number of procedures are available for quantitative determination of glucose, including quantitative determination of glucose in blood utilizing enzymes. However, these procedures are tyically not adaptable for in-vivo applications, and for the most part find difficulty in being adapted for even simple in-vitro determinations.

More recently, chemically modified electrodes have been applied to certain electrochemical sensing operations. In this connection, enzymes or other reagent proteins may be covalently attached to the surface of an electrode, and thereby prepare a simple electrode which may be utilized to conduct electrochemical determinations either amperometrically or potentiometrically. Accurate determinations may be achieved in either operational mode. The present invention utilizes an electrode system which an enzyme material is covalently bonded to a treated substrate surface, with the electrode being stable, rugged, and useful for bio-determinations. The substrate surface is oxidized iridium to which a silanized film is applied, and therafter a glucose oxidase layer is covalently bonded to the treated substrate surface. A protective coverlay in the form of a silicone rubber film is preferably applied to the covalently bonded enzyme material, with such films accommodating the transport of glucose and oxygen for proper and accurate quantitative determinations.

SUMMARY OF THE INVENTION

In accordance with the present invention, an electrode is provided for glucose sensing with the electrode functioning on an amperometric basis. The electrode comprises an iridium substrate having an oxidized surface to which a number of films are sequentially bonded—the first film being silanized gamma aminopropyltriethoxysilane, and the second film being glucose oxidase which is covalently bonded to the substrate. A coverlay film, such as a silicone rubber film is formed and/or applied over the outer surface of the glucose oxidase layer. The electrode system, when immersed in blood, provides a signal indicative of glucose concentration, and hence is useful as a blood glucose sensor in a variety of applications. One particularly useful application is in combination with a variable rate or programmable implantable insulin infusion pump. Variable rate implantable insulin infusion pumps are, of course, known at the present time, and electronic means are available for programming the activity of the pump so as to provide a desirable and appropriate level of blood insulin for the patient at all times. The program capability of the implantable infusion pump takes into account or otherwise accommodates the anticipated normal daily activity of the patient including ingestion of food and beverages, periods of exercise, periods of rest, and the like. The operation of the infusion pump including rate of delivery of insulin to the patient is controlled, at least in part, by the blood glucose sensor, with the sensor device providing an indication of the immediate glucose level in the blood of the patient.

Therefore, it is a primary object of the present invention to provide an improved electrode system which is particularly adapted for determining blood glucose levels or concentration in blood, and suitable for either in-vitro or in-vivo applications.

It is a further object of the present invention to provide an improved electrode means which is particularly desirable for determining blood glucose concentration on in-vitro or in-vivo applications, and wherein the sensing electrode is reliable, stable and rugged.

It is yet a further object of the present invention to provide a method and technique for the preparation of a glucose sensor which is particularly adapted for providing an electrical signal responsive to blood glucose levels, and wherein the sensor is suited for use in combination with a variable rate insulin infusion pump.

Other and further objects of the present invention will become apparent to those skilled in the art upon a study of the following specification and appended claims.

DESCRIPTION OF THE DRAWING

FIG. 1 is a plot of current versus glucose concentration utilizing the electrode system of the present invention.

DESCRIPTION OF THE PREFERRED EMBODIMENT

An iridium substrate is selected from a length of iridium filament having a diameter of from 2 to 5 mils, and with a generally rectangular flat foil flag secured to the distal end thereof. The foil flag is either square or rectangular, and preferably about 10 millimeters square. The iridium filament and its depending foil is then provided with an in-situ coating of iridium oxide through thermal treatment in an air atmosphere at a temperature of 700° C. While thermal iridium oxide layers are generally preferred, it will be appreciated that electrolytically prepared iridium oxide layers may also be successfully utilized. The oxide coated iridium substrate is then immersed in a solution of gamma aminopropyltriethoxysilane (30 volume percent) in hexane at 70° C. for one hour, to deposit a film of silanized alumina on the substrate. The silanized electrode is then rinsed with de-ionized water and treated with a 2.5% gluteraldehyde solution in a 7.4 pH phosphate buffer for a period of one hour at room temperature. The gluteraldehyde treated electrode is then rinsed and treated with an aqueous solution of glucose oxidase containing 140 units/cc in a 7.4 pH phosphate buffer solution. The exposure to glucose oxidase provides a covalently bonded film of glucose oxidase on the iridium/iridium oxide electrode.

EXAMPLE 1

A 2 mil iridium wire along with a 2 mil 10 mm square flag is immersed in hot 5M sulfuric acid to remove any surface oxide coating. The components are then degreased with acetone if necessary. The iridium wire is then spot-welded to the iridium flag electrode. The wire component is normally flattened on one end to enhance the bonding capability, with flattening being achieved by either a vise or by hammering. The surfaces to be welded together are, of course, clean and free of either surface oxide or grease. In order to prepare the welder electrodes, the working surfaces are initially cleaned with 500 grit sandpaper, and then wiped with acetone. A spot-welder having standard ⅛th inch diameter electrodes is appropriate for the operation, with 12-15 watt-seconds of energy being delivered on short-pulse intervals.

The welded iridium electrode is then dipped in saturated sodium bicarbonate, or alternatively, 0.1M KOH. The electrode is then heated in an oven with an air-atmosphere at a temperature of between 600° C. and 700° C. for one minute. Heating is accomplished in an alumina tray, with the electrode being positioned so that the flag foil portion is not in direct contact with the tray or the hot oven walls. The oxidized electrode is then removed from the heat zone and permitted to cool to room temperature over a period from 6 to 10 minutes.

The steps of dipping in sodium bicarbonate, heating and cooling are repeated until a uniform film of blueish-black iridium oxide is formed on the surface. Normally, 4 to 5 such repetition cycles are utilized.

After formation of the iridium oxide, the electrode is boiled in distilled water for a period of 30 minutes, and is then ready for the treatment with gamma aminopropyltriethoxysilane.

The treatment in silane includes immersion in a 30 volume percent of gamma aminopropyltriethoxysilane in hexane, with the solution heated to a temperature of 70° C. The immersion is continued for a period of one hour. Following removal from the silane solution, the silanized electrode is rinsed with de-ionized water, and thereafter immersed in a 2.5% glutaraldehyde solution in a 7.4 pH phosphate buffer for a period of one hour. The glutaraldehyde treatment operation is followed by rinsing in de-ionized water, and thereafter the electrode is immersed in an aqueous solution of glucose oxidase containing 140 units/cc in a 7.4 pH phosphate buffer solution. The phosphate buffers employed in this operation are preferably mixtures of monobasic and dibasic sodium phosphate having a concentration of about 0.1M, with the ratios adjusted so as to obtain a pH of 7.4.

In order to complete the preparation of the working electrode, a film of silicone rubber is applied over the surface of the glucose oxidase covalently bonded film. Specifically, silicone rubber available from Dow Chemical Corp. of Midland, Mich. available commercially under the code designation "Silicone Type A, Silastic Medical Adhesive" may be utilized. Such films having thicknesses ranging from between about 3 and 8 mils are useful, with a film thickness of about 5 mils being preferred. Such films, while protecting the surface of the glucose oxidase materials from direct exposure or contact with the blood, nevertheless provide a transport mechanism for both glucose and oxygen constituents of the blood.

The resulting electrode provides a strong EMF response to glucose. Specifically, the response of the electrode to concentration changes in glucose levels normally encountered in blood has been measured at approximately 90 mv/decade of glucose concentration change. Also, the iridium oxide surface can be reversably re-oxidized to iridium oxide with the oxidation current having likewise been found to be proportional to the glucose concentration. FIG. 1 is a plot of current versus glucose concentration utilizing the electrode system of the present invention. Current is expressed in $A \times 10^9$, with increasing concentration, and with glucose concentration being expressed in grams per deciliter. The current outputs were determined at room temperature utilizing a 7.4 pH phosphate buffer, 50 ml 0.1M $KH_2PO_4$ + 39.1 ml 0.1M NaOH + 8.8 g NaCl(the resulting solution is 0.15M in NaCl. The voltage is 0.031 versus a saturated calomel electrode.

The glucose oxidase electrode system is usable with respect to calomel, and also to silver/silver chloride half cells.

The electrode of the present invention provides advantages for in-vivo as well as in-vitro blood glucose level determinations. The electrical response, specifically the amperometric response, has been found to be specific to glucose concentration levels, and hence the electrode system has utility for use as a glucose determination means.

The glucose oxidase film is both rugged and durable, being covalently bonded to the electrode surface, with the other films used in conjunction with this composite film also having desirable adhesive and cohesive properties. The oxide surface formed on the iridium substrate is likewise desirable because of its porous nature, thereby further contributing to the stability, reliability, and ruggedness of the resultant product.

I claim:

1. Glucose sensor means for in-vivo generation of an electrical signal in response to the presence of glucose in the bloodstream and thereby electrically determining blood glucose concentrations, said sensor means comprising an iridium substrate with an in-situ oxidized outer surface of iridium oxide to which are bonded first and second superposed films, said first film being bonded to said iridium oxide surface and consisting essentially of silanized gamma aminopropyltriethoxysilane, and with said second film consisting essentially of glucose oxidase and being covalently bonded in-situ onto said first film.

2. Glucose sensor means for in-vivo generation of an electrical signal in response to the presence of glucose in the bloodstream and thereby electrically determining blood glucose concentrations and comprising an iridium base substrate having an in-situ coating of iridium oxide on the surface thereof, and with a first film adherently bonded thereto and a second film adherently and serially bonded onto the surface of said first film, said first film consisting essentially of a silanized layer of gamma aminopropyltriethoxysilane and said second film consisting of essentially glucose oxidase covalently bonded to the surface of said first film, and with a silicone rubber film being applied to the outer surface of said glucose oxidase film.

3. The method of preparing a glucose sensor for electrically determining blood glucose concentrations including the steps of:

(1) oxidizing the surface of an iridium base to form a layer of in-situ oxide thereon;

(2) thereafter exposing the iridium oxide surface to a solution of gamma aminopropyltriethoxysilane to prepare a silanized film thereon;

(3) thereafter treating the silanized coating with an acqueous solution of glucose oxidase to form a covalently bonded film of glucose oxidase on the silanized film; and (4) thereafter treating the glucose oxidase film through application of a film of silicone rubber to the surface thereof.

4. The method as set forth in claim 3 being particularly characterized in that said in-situ coating of iridium oxide is formed by thermally treating an iridium substrate to an atmosphere of air at a temperature of 600°–700° C. for a period of about one minute, with the resulting composite film being cooled and thereafter dipped in an aqueous solution of KOH.

5. The method as set forth in claim 4 being particularly characterized in that said aqueous solution of KOH is at a concentration level of about 0.1M KOH.

6. The method as set forth in claim 5 wherein said heating, cooling and dipping steps are repeated until a uniform surface layer of blue-black layer of $IrO_2$ is formed.

* * * * *